(12) United States Patent
Barone et al.

(10) Patent No.: US 7,026,114 B1
(45) Date of Patent: Apr. 11, 2006

(54) METHODS AND COMPOSITIONS FOR MONITORING POLYMER ARRAY SYNTHESIS

(75) Inventors: Anthony D. Barone, Santa Clara, CA (US); Glenn H. Mc Gall, Mountain View, CA (US); Evelyn Chai, Foster City, CA (US); Nam Quoc Ngo, Campbell, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 08/574,461

(22) Filed: Nov. 30, 1995

Related U.S. Application Data

(60) Provisional application No. 60/003,726, filed on Sep. 13, 1995.

(51) Int. Cl.
*C12Q 1/68* (2006.01)
*G01N 33/543* (2006.01)
*A61K 38/00* (2006.01)
*C07H 21/04* (2006.01)

(52) U.S. Cl. ............................ 435/6; 435/4; 435/287.1; 435/288.7; 435/DIG. 1; 435/DIG. 34; 435/DIG. 49; 436/518; 530/333; 530/334; 530/335; 536/24.3; 536/25.3; 536/25.31; 536/25.32

(58) Field of Classification Search ............... 536/23.1, 536/25.3, 25.32, 24.3, 25.31; 435/7.1, 6, 435/DIG. 1, DIG. 2, DIG. 14, DIG. 15, DIG. 16, 435/DIG. 17, DIG. 18, DIG. 46, DIG. 49; 435/4, 287.1, 288.7, DIG. 34; 436/518; 530/333, 334, 335

See application file for complete search history.

(56) References Cited

U.S. PATENT DOCUMENTS

| | | | | |
|---|---|---|---|---|
| 5,143,854 | A | | 9/1992 | Pirrung et al. ............... 436/518 |
| 5,472,672 | A | * | 12/1995 | Brennan ..................... 422/131 |
| 5,474,796 | A | | 12/1995 | Brennan |
| 5,556,961 | A | | 9/1996 | Foote et al. |
| 5,650,489 | A | * | 7/1997 | Lam et al. .................. 530/334 |
| 5,679,773 | A | * | 10/1997 | Holmes ....................... 530/334 |
| 5,843,655 | A | * | 12/1998 | McGall ........................ 435/6 |
| 6,238,862 | B1 | * | 5/2001 | McGall et al. ................ 435/6 |

OTHER PUBLICATIONS

Pease AC, et al, (1994) Light-generated oligonucleotide arrays for rapid DNA sequence analysis. Proc.Natl.Acad-.Sci.U.S.A. 91:5022-5026.*
Reynolds MA, et al, (1992) A non-nucleotide-based linking method for the preparation of psoralen-derivatized methylphosphonate oligonucleotides. Bioconjug.Chem. 3: 366-374.*
Silverstein and Bassler, Spectrophotmetric Identification of Organic Compounds, John Wiley and Sons, New York pp. 161-162, 1963.*
Fodor et al. Light-Directed, spatially addressable parallel chemical synthesis. Science 251:767-773, Feb. 15, 1991.*
Fodor et al. (1991) *Science* 251:767-777.
Frank and Doring (1988) *Tetrahedron* 44:6031-6040.
*Advanced Organic Chemistry: Reactions, Mechanisms and Structure*, Fourth Edition (Mar. 1992), Chapter 4, John Wiely and Sons.
Hochuli (1989) *Chemische Industrie* 12:69-70.
Hochuli (1990) "Purification of Recombinant Proteins with Metal Chelate Absorbent" In: *Genetic Engineering, Principle and Methods*, Setlow (ed.) Plenum Press, N.Y. 12:87-98.
Barone et al. (1984) *Nucleic Acids Research* 12:4051.
Reynolds et al. (1992) *Bioconjugate Chemistry* 3:366.
Pease et al. (1994) *Proc. Natl. Acad. Sci. USA* 91:5022.
Cho et al., "An Unnatural Biopolymer," *Science*, 261:1303-1305 (1993).
Nestler et al., "A General Method for Molecular Tagging of Encoded Combinatorial Chemistry Libraries," *J. Org. Chem.*, 59:4723-4724 (1994).

* cited by examiner

*Primary Examiner*—Padmashri Ponnaluri
(74) *Attorney, Agent, or Firm*—Banner & Witcoff, Ltd.

(57) ABSTRACT

VLSIPS™ manufacturing processes are of increasing commercial importance. The present invention provides methods and compositions for monitoring the efficiency and quality of polymer synthesis in VLSIPS™ arrays. Methods for monitoring polymer synthesis in an array on a substrate are provided. Monoisomeric labels for the labeling of synthetic polymer arrays are provided. Methods and compositions for post-synthetically labeling polymers in polymer arrays are also provided.

34 Claims, 3 Drawing Sheets

2  R = H
3  R = DMT

4

5  $R^1$ = H, $R^2$ = H
6  $R^1$ = pivaloyl, $R^2$ = H
7  $R^1$ = —P(N(iPr)$_2$)(OCH$_2$CH$_2$CN), $R^2$ = pivaloyl

METHODS AND COMPOSITIONS FOR MONITORING POLYMER ARRAY SYNTHESIS

CROSS REFERENCE TO RELATED APPLICATIONS

This Application claims the benefit of the U.S. Provisional Application by Barone et al. (U.S. Ser. No. 60/003,726) filed Sep. 13, 1995.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

Methods of forming large arrays of oligonucleotides, peptides and other polymers on a solid substrate are known. Pirrung et al., U.S. Pat. No. 5,143,854 (see also PCT Application No. WO 90/15070), McGall et al., U.S. Ser. No. 06/440742, Chee et al., SN PCT/US94/12305, and Fodor et al., PCT Publication No. WO 92/10092 describe methods of forming vast arrays of peptides, oligonucleotides and other polymers using, for example, light-directed synthesis techniques.

In the Fodor et al. PCT application, methods are described for using computer-controlled systems to direct polymer array synthesis. Using the Fodor approach, one heterogeneous array of polymers is converted, through simultaneous coupling at multiple reaction sites, into a different heterogeneous array. See also, U.S. Ser. No. 07/796,243 and U.S. Ser. No. 07/980,523 and Fodor et al. (1991) *Science*, 251: 767–777.

The arrays are typically placed on a solid surface with an area less than 1 inch$^2$, although much larger surfaces are optionally used.

More recently, U.S. applications U.S. Ser. No. 06/440,742, U.S. Ser. No. 08/284,064, U.S. Ser. No. 08/143,312, U.S. Ser. No. 08/082,937 and PCT application (designating the United States) SN PCT/U594/12305, describe methods of making arrays of oligonucleotide and oligonucleotide analogue probes, e.g., to check or determine a partial or complete sequence of a target nucleic acid, or to detect the presence of a nucleic acid containing a specific oligonucleotide sequence. U.S. application Ser. No. 08/327,687 and U.S. application Ser. No. 06/440,742 describe methods of creating libraries of nucleic acid probes for the analysis of nucleic acid hybridization, and for screening nucleic acid binding molecules, e.g., as potential therapeutic agents.

Additional methods applicable to polymer synthesis on a substrate are described in co-pending Applications U.S. Ser. No. 07/980,523, filed Nov. 20, 1992, and U.S. Ser. No. 07/796,243, filed Nov. 22, 1991, incorporated herein by reference for all purposes. In the methods disclosed in these applications, reagents are delivered to the substrate by flowing or spotting polymer synthesis reagents on pre defined regions of the solid substrate. In each instance, certain activated regions of the substrate are physically separated from other regions when the monomer solutions are delivered to the various reaction sites, e.g., by means of grooves, wells and the like.

SUMMARY OF THE INVENTION

VLSIPS™ procedures are of increasing commercial importance, providing powerful compositions and methods, e.g., for detecting genetic disorders, screening potential therapeutics, facilitating basic research and rapid sequencing of nucleic acids. Accordingly, the manufacturing processes which produce VLSIPS™ arrays benefit from quality control and synthesis optimization methods for measuring and improving the efficiency of polymer and polymer array synthesis and coupling of monomers and polymers to solid substrates.

The present invention provides methods and compositions to monitor the synthesis and coupling of monomers and polymers to solid substrates, e.g., in VLSIPS™ arrays. The methods typically operate by incorporating a detectable label (typically an isomeric label, e.g., as provided by the compositions herein) into the polymers of an array. The polymers are cleaved from the array, and the efficiency of polymer synthesis assessed by monitoring the detectable label in an appropriate assay.

In one class of embodiments, the present invention provides a method of monitoring polymer array synthesis on a solid substrate by providing a preselected array of labeled polymers connected to cleavable linkers on a solid substrate, cleaving the array of labeled polymers from the solid substrate by cleaving the cleavable linkers, thereby creating labeled unbound polymers, and detecting the labeled unbound polymers. In this embodiment, the labeled polymers each typically comprise a single isomeric label, although any detectable label can also be used. The polymers cleaved from the array are separated by physical properties such as size and/or charge, using known analytical techniques such as HPLC, standard column chromatography (anion, cation, size exclusion, etc.), gel-electrophoresis, centrifugation, capillary gel electrophoresis and the like.

The methods are generally suitable to any polymer array, regardless of the type of polymer. Thus, the efficiency of synthesis for biological polymers such as proteins, nucleic acids, antigens, and venoms are monitored using the above method. Non-biological polymers such as carbon chains, vinyls, alcohols, and other polymers are similarly monitored. The polymer array is typically provided by synthesizing the array on the solid substrate, but the array can also be provided by synthesizing the polymers to be attached to the array in solution, and subsequently attaching the polymers to pre-selected sites in the array.

In a second class of embodiments, the invention provides a method of measuring and improving the synthesis of polymer arrays, by synthesizing an array of polymers on a solid support by a first synthesis protocol, creating a reference array of polymers; synthesizing an array of polymers on a solid support by a second synthesis protocol, wherein the second synthesis protocol is different than the first synthesis protocol, thereby creating a test array of polymers; cleaving separately the reference array of polymers and the test array of polymers, thereby creating cleaved reference polymers and cleaved test polymers; detecting the cleaved test polymers and the cleaved reference polymers, and comparing the cleaved test polymers to the cleaved reference polymers. By repeating the process and altering different synthesis parameters between the test and the reference array of polymers, the optimal method of synthesizing a particular array is determined.

Typically, the polymers of an array comprise a detectable label to facilitate analysis of the cleaved polymers, although the polymers themselves are also detectable, and the method can, therefore, be performed without incorporating a detectable label. Where the method used for detecting the label discriminates between optical isomers of a label (e.g., HPLC) the label will most often comprise a single optical isomer. Although it is most preferred that a single synthetic parameter is altered for the test polymers relative to the control polymers, multiple parameters can be altered in each synthetic protocol. Once again, the method is generally applicable to biological and artificial polymers, each of which are typically connected to a solid substrate by a cleavable linker.

The methods of the present invention are typically performed using a detectable monomeric monoisomeric polymer synthesis reagent with the structure A-B, wherein A comprises a detectable chromogenic moiety and B comprises a polymer integration element. The polymer integration element typically includes a group which can be joined to one end of the polymer, or incorporated into the polymer as it is synthesized (i.e., as a monomeric unit of the polymer). The precise nature of the integration element depends on the polymer which the detectable moiety is to be integrated into. For instance, where the polymer is a peptide, the integration element will typically comprise an amino or a carboxy group, or both, similar to the amino acids which comprise the peptide. Similarly, where the polymer is an oligonucleotide, the polymer will typically comprise a phosphate or hydroxyl, or both, similar to the nucleotides which constitute the oligonucleotide polymer. The chromogenic moiety is most typically a fluorophore, although other chromogenic agents are also suitable.

In one embodiment, the polymer synthesis reagent is a nucleic acid synthesis reagent, and B (the polymer integration element) comprises the structure

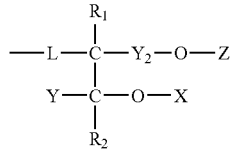

wherein

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation;

$R_1$ is selected from the group consisting of hydrogen, alkyl, and aryl;

$R_2$ is selected from the group consisting of hydrogen, alkyl, and aryl;

X is a nucleic acid integration element comprising a phosphorous atom;

Y is selected from the group consisting of hydrogen, alkyl, and aryl;

$Y_2$ is an alkyl chain; and

Z comprises a protecting group.

In one class of preferred embodiments, the polymer synthesis reagent is a nucleic acid synthesis reagent, and B (the polymer integration element) comprises the structure

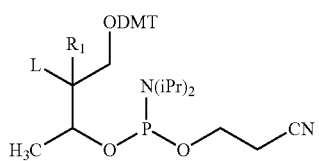

wherein

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation; and $R_1$ is selected from the group consisting of hydrogen, alkyl, and aryl.

This polymer integration element is typically joined to a fluorophore.

In another class of preferred embodiments, the invention provides an array of polymers, such as an array of oligonucleotides or proteins, or non-biological polymers, with a monoisomeric detectable label incorporated into each polymer. For instance, in one embodiment where the array is an oligonucleotide, the invention provides an array of oligonucleotides attached to a solid substrate, wherein the label is a monoisomeric label comprising the structure wherein F comprises a fluorescent group;

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation;

$R_1$ is selected from the group consisting of hydrogen, alkyl, and aryl;

$R_2$ is selected from the group consisting of hydrogen, alkyl, and aryl;

X is a nucleotide, nucleic acid or a cleavable linker;

Y is selected from the group consisting of hydrogen, alkyl, and aryl;

$Y_2$ is an alkyl chain; and

Z is a nucleotide or nucleic acid.

In one preferred group of embodiments, the nucleic acid synthesis reagent has the structure wherein $R_1$ is selected from the group consisting of alkyl, aryl, and hydrogen; $R_2$ is selected from the group consisting of alkyl, and aryl; and FL is a fluorescent moiety.

An example compound is fluorescein phosphoramidite 7.

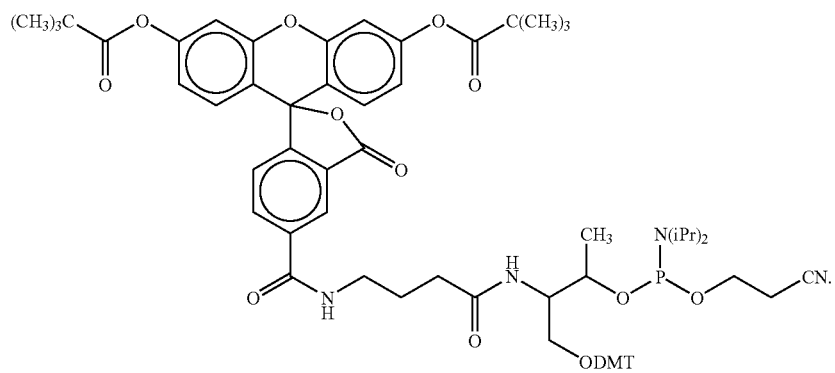

In another preferred group of embodiments, the reagent has the structure

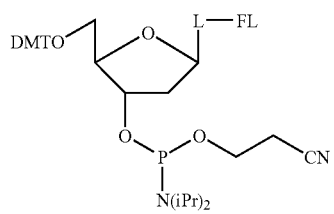

wherein

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation.

Most typically, the polymer arrays of the invention further comprise cleavable linkers, often located proximal to the substrate which the array is formed upon, to facilitate cleavage of the polynucleotide from the array.

In a preferred embodiment of the invention, methods of post-synthetically labeling an oligonucleotide array are provided. In these methods, a polymer array which comprises a plurality of polymers is provided, wherein each polymer in the array, or a plurality of polymers in the array, include a labeling site to which a detectable label such as a fluorophore is attached.

Most typically in this preferred embodiment, the polymers in the array are synthesized on labeling linkers, which are most typically attached to cleavable linkers proximal to the surface upon which the array is synthesized. The labeling linkers include attachment sites for the detectable label. During polymer synthesis the labeling linker includes a protected site for the attachment of the detectable label which is deprotected at a defined point in the synthesis of the array (typically after the polymers in the array are completely synthesized, and often after the polymers are cleaved from the array at the cleavable linker) so that the detectable moiety can be attached. For instance, where the detectable reagent is a fluorescent phosphoramidite, the protected site on the labeling linker will typically comprise an oxygen with which the phosphate on the phosphoramidite will react to form a phosphodiester linkage (i.e., after the oxygen is deprotected). DMT is a preferred protecting group, although many others are also suitable, depending on the nature of the group to be protected, the polymer and the detectable moiety.

The post-synthetic labeling linker used in the method typically has a site for polymer elongation, a site for attaching a polymer to a substrate and an attachment site for attaching a detectable label. Preferred labeling linkers are described herein. In general, where the labeling linker is a nucleic acid synthesis reagent, the labeling linker has the structure

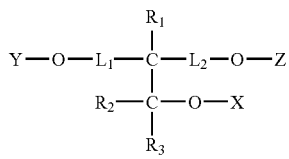

wherein:

$R_1$ is selected from the group consisting of hydrogen, alkyl and aryl;

$R_2$ is selected from the group consisting of hydrogen, alkyl and aryl;

$R_3$ is selected from the group consisting of hydrogen, alkyl and aryl;

$L_1$ is a linking chain selected from the group of alkyl linking chains consisting of an alkyl linking chain from 1 to 30 carbons in length, wherein one or more carbon is optionally substituted with a heteroatom selected from the group consisting of N, S, O and P, and wherein the alkyl linking group optionally includes one or more sites of unsaturation, and an alkyl linking chain from 1 to 30 carbons in length, wherein one or more carbon is optionally replaced with a heteroatom selected from the group consisting of N, S, O and P, and wherein the alkyl linking group optionally includes one or more sites of unsaturation;

$L_2$ is a linking chain selected from the group of alkyl linking chains consisting of an alkyl linking chain from 1 to 30 carbons in length, wherein one or more carbon is optionally substituted with a heteroatom selected from the group consisting of N, S, O and P, and wherein the alkyl linking group optionally includes one or more sites of unsaturation, and an alkyl linking chain from 1 to 30 carbons in length, wherein one or more carbon is optionally replaced with a heteroatom selected from the group consisting of N, S, O and P, and wherein the alkyl linking group optionally includes one or more sites of unsaturation;

Y is selected from the group consisting of a dimethoxytrityl protecting group and a photoclevable protecting group;

Z is selected from the group consisting of a dimethoxytrityl (DMT) protecting group and a photoclevable protecting group; and X is a nucleic acid integration element comprising a phosphorous atom.

DEFINITIONS

Figure 1:
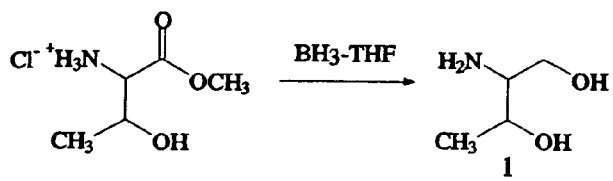
FIG. 1 provides a synthesis scheme for the synthesis of fluorescent amidite (7).
Figure 1:
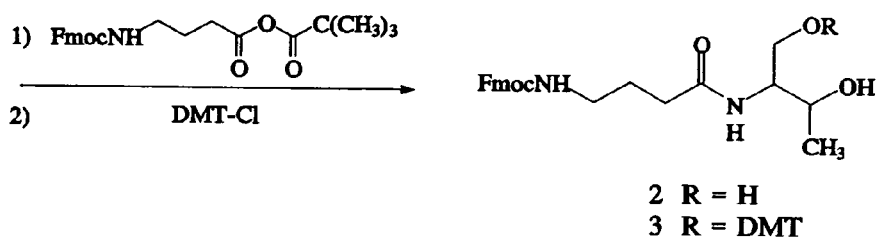
Figure 1:
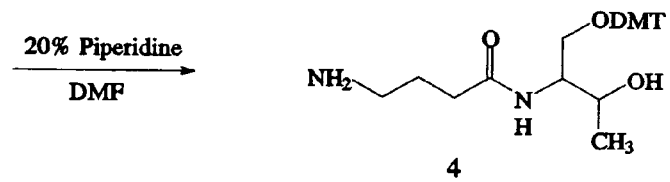
Figure 1:
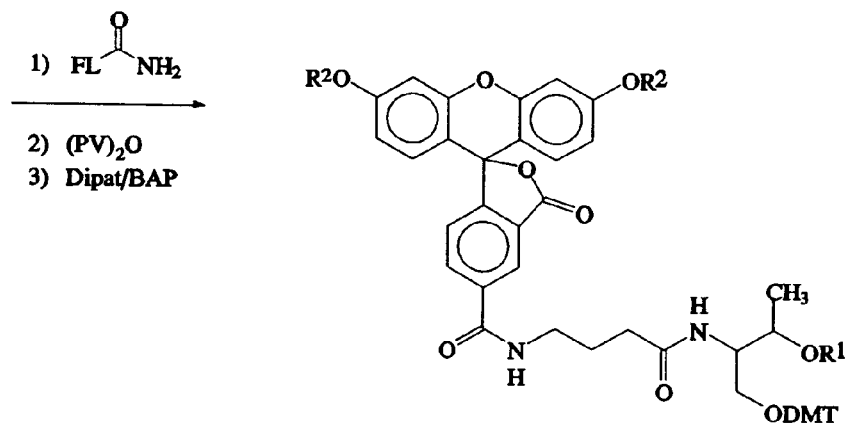

Unless defined otherwise, technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) and March (March, *Advanced Organic Chemistry Reactions, Mechanisms and Structure* 4th ed J. Wiley and Sons (New York, 1992) provides one of skill with a general guide to many of the terms used in this invention.

Although one of skill will recognize many methods and materials similar or equivalent to those described herein which can be used in the practice of the present invention, the preferred methods and materials are described. For purposes of the present invention, the following terms are defined below.

An "activating agent" refers to those groups which, when attached to a particular functional group or reactive site, render that site more reactive toward covalent bond formation with a second functional group or reactive site. For example, the group of activating groups which are useful for a carboxylic acid include simple ester groups and anhydrides. The ester groups include alkyl, aryl and alkenyl esters, and in particular such groups as 4-nitrophenyl, N-succinimidyl and pentafluorophenyl. Other activating agents are known to those of skill in the art.

An "alkyl" or "lower alkyl" group refers to a saturated hydrocarbon or hydrocarbon radical which includes a straight or branched chain (for example, methyl, ethyl, isopropyl, t-amyl, or 2,5-dimethylhexyl). Preferred alkyl groups are those containing 1 to 15 carbon atoms or more preferably contain 1–6 carbon atoms unless otherwise indicated (e.g., for certain alkyl linking groups described herein, the optimal length of the alkyl chain is from 1 to 30 carbons in length). When "alkyl" or "alkylene" is used to refer to a linking group or a spacer moiety, it is taken to be a group having at least two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. The hydrocarbon chain is optionally substituted with heteroatoms such as N, O, P, and S, or similarly, one or more carbons can be replaced with a heteroatom. The alkyl chain optionally includes one or more site of unstauration (e.g., a C=C bond).

An "aryl" group as used herein, refers to an aromatic substituent which is a single or multiple ring structure, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl). As used herein, the term "aralkyl" refers to an alkyl group bearing an aryl substituent (for example, benzyl, phenylethyl, 3-(4-nitrophenyl)propyl, and the like). All numerical ranges in this specification and claims are intended to be inclusive of their upper and lower limits.

The term "capping" in the context of synthesizing an array of polymers refers to a step in which unreacted groups that fail to condense and successfully couple with the next polymer synthesis reagent (e.g., a monomer such as a phosphoramidite or amino acid) are blocked. This insures that subsequent reactions proceed only by propagating chains of desired sequence. For instance, capping typically involves the acetylation of 5'-hydroxyl functions on oligonucleotides. This is accomplished, e.g., using acetic anhydride catalyzed by 4-dimethylaminopyridine (DMAP). Other reagents known to those of skill in the art are also suitable.

The term "label" refers to a composition detectable by spectroscopic, photochemical, biochemical, immunochemical, or chemical means. For example, useful labels include $^{32}$P, $^{35}$S, fluorescent dyes, chromophores, electron-dense reagents, enzymes (e.g., as commonly used in an ELISA), biotin, dioxigenin, or haptens and proteins for which antisera or monoclonal antibodies are available.

A "labeling linker" is a polymer synthesis reagent which contains a labeling site and a polymer attachment site. The chemical nature of the polymer attachment site is selected to be compatible with the polymer to be synthesized. Thus, where the polymer is an oligonucleotide, the polymer attachment site comprises an oxygen or phosphate for attachment to the 3' OH or 5' phosphate of the oligonucleotide. A "polymer labeling site" or "labeling site" in the context of the labeling linker, or polymers in a polymer array is a chemical site which is reactive with the reactive groups in a label or synthetic labeling reagent. Thus, the precise chemical composition of the site depends on the chemical nature of the reactive site on the label. Thus, where the label comprises a phosphate, the labeling site would optionally include an oxygen (e.g., a double-bond O or hydroxyl), or other phosphate-reactive moiety. It is assumed that one of skill is familiar with many chemical sites which react to form a chemical bond, including those which occur during nucleic acid synthesis and polynucleotide synthesis. In many embodiments, the labeling site is protected with a protecting group. It is generally understood that nucleic acid reagents carry a protected phosphate or hydroxyl group in order to form a phosphodiester linkage.

In preferred embodiments, the labeling linker comprises two polymer attachment sites, such that the polymer is extended from the labeling linker. In many embodiments, the labeling linker is attached to a cleavable linker at one end, and to a polymer at the other end. Thus, in this embodiment, the labeling linker has three attachment sites: one site for forming a chemical bond to the cleavable linker, one site for forming a chemical bond to a monomer from which the polymer is elongated, and one site for forming a chemical bond to the detectable label.

A "nucleic acid reagent" is a molecule which can be used for oligonucleotide synthesis. The molecules typically carry protected phosphates and/or protected oxygen moieties. For instance, nucleic acid reagents include nucleotide reagents, nucleoside reagents, nucleoside phosphates, nucleoside-3'-phosphates, nucleoside phosphoramidites, phosphoramidites, nucleoside phosphonates, phosphonates, methyl phosphonates, O-methyl phosphates etc. It is generally understood that nucleotide reagents carry a protected phosphate or hydroxyl group in order to form a phosphodiester linkage.

A "nucleoside" is a pentose glycoside in which the aglycone is a heterocyclic base; upon the addition of a phosphate group the compound becomes a "nucleotide". The major biological nucleosides are β-glycoside derivatives of D-ribose or D-2-deoxyribose. Nucleotides are phosphate esters of nucleosides which are generally acidic in solution due to hydroxy groups on the phosphate. The nucleosides of the polymeric nucleic acids DNA and RNA are connected together via phosphate units attached to the 3' position of one pentose and the 5' position of the next pentose. Nucleotide analogues and/or nucleoside analogues are molecules with structural similarities to the naturally occurring nucleotides or nucleosides. Means of converting a nucleoside to a phosphoramidite are well known to those of skill in the art. See, for example, Atkinson et al., chapter 3, in Gait, ed., *Oligonucleotide Synthesis: A Practical Approach* (IRL Press, Washington, D.C., 1984), which is incorporated herein by reference, and McBride and Caruthers, *Tetrahedron Lett.*, 24: 245 (1983). See, also Blackburn and Gait (eds) (1990) *Nucleic Acids in Chemistry and Biology* IRL press, NY.

A "nucleic acid" is a deoxyribonucleotide or ribonucleotide polymer in either single- or double-stranded form, and unless otherwise limited, encompasses known analogs of natural nucleotides that function in a manner similar to naturally occurring nucleotides (See, copending application U.S. Ser. No. 06/440742 for a description of nucleic acid analogues).

An "oligonucleotide" is a nucleic acid polymer composed of two or more nucleotides or nucleotide analogues. An oligonucleotide can be derived from natural sources but is often synthesized chemically. It is of any size. Copending application U.S. Ser. No. 06/440742 describes a variety of oligonucleotide analogues.

A "polymer" refers to a chain of monomers, typically connected through chemical or electrostatic interactions. Monomers include, but are not limited to, biological monomers such as L-amino acids, D-amino acids, synthetic amino acids, nucleotides, nucleosides, phosphoramidites, and carbohydrates, as well as non-biological monomers which are connected to form polymers. As used herein, monomer refers to any unit of a polymer. For example, dimers of the 20 naturally occurring L-amino acids form 400 monomeric units for synthesis of polypeptides. Different monomeric units are optionally used at any site in the polymer. Each monomeric unit optionally includes protected members which are optionally modified after polymerization. Biological polymers include, but are not limited to, agonists and antagonists of cell membrane receptors, toxins and venoms, viral epitopes, hormones (e.g., opiates, steroids, etc.), hormone receptors, peptides, retro-inverso peptides, polymers of α-, β-, or ω-amino acids (D- or L-), enzymes, enzyme substrates, cofactors, drugs, lectins, sugars, nucleic acids (both linear and cyclic polymer configurations), oligosaccharides, proteins, phospholipids and antibodies. Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates are also included. Other polymers will also be apparent to one of skill upon review of this disclosure.

A "peptide" or "polypeptide" or "protein" refers to a polymer of amino acids. Typically the monomers are alpha amino acids which are joined together through amide bonds. In the context of this specification, the L-optical isomer and the D-optical isomer are both contemplated, unless otherwise indicated. Standard abbreviations for amino acids are used (e.g., P for proline). These abbreviations are included, e.g., in Stryer, *Biochemistry*, Third Edition, 1988.

A "polymer array" is a spatially defined pattern of polymers on a solid support. A "preselected array of polymers" is a spatially defined pattern of polymers on a solid support which is designed before being constructed (i.e., the arrangement of polymers on solid substrate during synthesis is deliberate, and not random).

A "protecting group" as used herein, refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y., 1991, which is incorporated herein by reference. The proper selection of protecting groups for a particular synthesis is governed by the overall methods employed in the synthesis. For example, in "light-directed" synthesis, discussed herein, the protecting groups are typically photolabile protecting groups such as NVOC, MeNPoc, and those disclosed in co-pending Application PCT/US93/10162 (filed Oct. 22, 1993), incorporated herein by reference. In other methods, protecting groups are removed by chemical methods and include groups such as FMOC, DMT and others known to those of skill in the art.

The term "protected amino acid" refers to an amino acid, typically an α-amino acid having either or both the amine functionality and the carboxylic acid functionality suitably protected by one of the groups described above. Additionally, for those amino acids having reactive sites or functional groups on a side chain (i.e., serine, tyrosine, glutamic acid), the term "protected amino acid" is meant to refer to those compounds which optionally have the side chain functionality protected as well.

A "solid substrate" has a fixed organizational support matrix, such as silica, polymeric materials, or glass. In some embodiments, at least one surface of the substrate is partially planar. In other embodiments it is desirable to physically separate regions of the substrate to delineate synthetic regions, for example with trenches, grooves, wells or the like. Example of solid substrates include slides, beads and polymeric chips. A solid support is "functionalized" to permit the coupling of monomers used in polymer synthesis. For example, a solid support is optionally coupled to a nucleoside monomer through a covalent linkage to the 3'-carbon on a furanose. Solid support materials typically are unreactive during polymer synthesis, providing a substratum to anchor the growing polymer. Solid support materials include, but are not limited to, glass, polacryloylmorpholide, silica, controlled pore glass (CPG), polystyrene, polystyrene/latex, and carboxyl modified teflon. The solid substrates are biological, nonbiological, organic, inorganic, or a combination of any of these, existing as particles, strands, precipitates, gels, sheets, tubing, spheres, containers, capillaries, pads, slices, films, plates, slides, etc. depending upon the particular application. In light-directed synthetic techniques, the solid substrate is often planar but optionally takes on alternative surface configurations. For example, the solid substrate optionally contains raised or depressed regions on which synthesis takes place. In some embodiments, the solid substrate is chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid substrate materials will be readily apparent to those of skill in the art. Preferably, the surface of the solid substrate will contain reactive groups, such as carboxyl, amino, hydroxyl, thiol, or the like. More preferably, the surface is optically transparent and has surface Si—OH functionalities, such as are found on silica surfaces. A substrate is a material having a rigid or semi-rigid surface. In spotting or flowing VLSIPS™ techniques, at least one surface of the solid substrate is optionally planar, although in many embodiments it is desirable to physically separate synthesis regions for different polymers with, for example, wells, raised regions, etched trenches, or the like. In some embodiments, the substrate itself contains wells, trenches, flow through regions, etc. which form all or part of the regions upon which polymer synthesis occurs.

DETAILED DESCRIPTION

The present invention provides methods and compositions for monitoring and optimizing polymer array synthesis. The methods presented herein typically proceed by incorporating a detectable label into polymers in arrays on a solid substrate. The labeled polymers in the array are then cleaved from the solid surface, typically by cleaving a cleavable linker which attaches the polymers of the array to the solid surface. The polymers are then analyzed by monitoring the detectable label in an appropriate assay, i.e., determined by the label. A variety of analytic assays such as HPLC, gel electrophoresis or capillary gel electrophoresis (CGE) are contemplated.

One aspect of interest during the manufacture of a VLSIPS™ array is the efficiency of polymer synthesis in the array, including the length distribution of synthesized species and the presence, nature and extent of truncated species. Measuring the size and/or electrostatic charge of polymers cleaved from an array, and comparing the measurements to the predicted size and/or charge of the polymers provides a measure of the efficiency of polymer synthesis. Varying synthesis protocols and comparing the resulting polymer arrays also provides an efficient empirical strategy for optimizing the procedures for producing polymer arrays.

The effect of environmental, synthetic, or experimental conditions on polymer arrays is also determined by the methods presented herein. In one class of embodiments, a reference polymer array and a test polymer array are synthesized using identical procedures. The reference polymer array is cleaved from the solid support after synthesis and analyzed as described herein. The test polymer array is subjected to defined additional environmental conditions such as immersion in an aqueous, acidic, or basic solution, or exposure to nucleases or peptidases, and then analyzed. By comparing the polymers of the array (or of identical sets of arrays) before and after exposure to the defined environmental conditions, the stability and durability of the array is determined.

Although essentially any detectable label can be used, in preferred embodiments the label is monoisomeric, i.e., the label has only a single optical isomer. The use of monoisomeric labels avoids any ambiguity in monitoring the size or charge of polymers in an array caused by having an enantiomeric or diastereomeric label. The use of mono-isomeric labels is particularly useful when the detection method is extremely sensitive. For instance, the use of mono-isomeric labels when the detection method is HPLC is particularly preferred.

Synthesis of Polymer Arrays

The present invention relates to the creation of labeled polymer arrays. The synthesis of polymer arrays generally is known. The development of very large scale immobilized polymer synthesis (VLSIPS™) technology provides methods for arranging large numbers of polymer probes in very small arrays. Pirrung et al., U.S. Pat. No. 5,143,854 (see also PCT Application No. WO 90/15070), McGall et al., Ser. No. 06/440,742, Chee et al. SN PCT/US94/12305, and Fodor et al., PCT Publication No. WO 92/10092 describe methods of forming vast arrays of peptides, oligonucleotides and other polymers using, for example, light-directed synthesis techniques. See also, U.S. Ser. No. 07/796,243 and 07/980,523, Fodor et al. (1991) *Science* 251:767–777, and Ser. No. 08/327,687.

As described above, diverse methods of making polymer arrays are known; accordingly no attempt is made to describe or catalogue all known methods. For exemplary purposes, light directed VLSIPS™ methods are briefly described below. One of skill will understand that alternate methods of creating polymer arrays, such as spotting and/or flowing reagents over defined regions of a solid substrate, bead based methods and pin-based methods are also known and applicable to the present invention (See, Holmes et al. (filed Jan. 17, 1995) U.S. Ser. No. 08/374,492).

Light directed VLSIPS™ methods are found, e.g., in U.S. Pat. No. 5,143,854. The light directed methods discussed in the '854 patent typically proceed by activating predefined regions of a substrate or solid support and then contacting the substrate with a preselected monomer solution. The predefined regions are activated with a light source, typically shown through a photolithographic mask. Other regions of the substrate remain inactive because they are blocked by the mask from illumination. Thus, a light pattern defines which regions of the substrate react with a given monomer. By repeatedly activating different sets of predefined regions and contacting different monomer solutions with the substrate, a diverse array of polymers is produced on the substrate. Other steps, such as washing unreacted monomer solution from the substrate, are used as necessary.

The surface of a solid support is typically modified with linking groups having photolabile protecting groups (e.g., NVOC or MeNPOC) and illuminated through a photolithographic mask, yielding reactive groups (e.g., typically hydroxyl groups when the polymer array is an oligonucleotide array) in the illuminated regions. For instance, during oligonucleotide synthesis, a 3'-O-phosphoramidite (or other nucleic acid synthesis reagent) activated deoxynucleoside (protected at the 5'-hydroxyl with a photolabile group) is then presented to the surface and coupling occurs at sites that were exposed to light in the previous step. Following capping, and oxidation, the substrate is rinsed and the surface illuminated through a second mask, to expose additional hydroxyl groups for coupling. A second 5'-protected, 3'-O-phosphoramidite activated deoxynucleoside (or other monomer as appropriate) is then presented to the resulting array. The selective photodeprotection and coupling cycles are repeated until the desired set of oligonucleotides (or other polymers) is produced.

Making Polymers to be Coupled into Arrays

As described above, several methods for the synthesis of polymer arrays are known. In preferred embodiments, the polymers are synthesized directly on a solid surface as described above. However, in certain embodiments, it is useful to synthesize the polymers and then couple the polymers to the solid substrate to form the desired array. In these embodiments, polymers are synthesized (in vitro or in vivo, in solution, or using solid phase chemistry) and then attached to a solid substrate in a desired pattern to form the desired array on the solid substrate.

Molecular cloning and expression techniques for the synthesis of biological and synthetic polymers in solution are known in the art. A wide variety of cloning and expression and in vitro methods suitable for the construction of polymers are well-known to persons of skill. Examples of techniques and instructions sufficient to direct persons of skill through many cloning exercises for the expression and purification of biological polymers (DNA, RNA, proteins) are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

Examples of techniques sufficient to direct persons of skill through in vitro methods of polymer synthesis in solution, including enzymatic methods such as the polymerase chain reaction (PCR), the ligase chain reaction (LCR), Qβ-replicase amplification (QBR), nucleic acid sequence based amplification (NASBA), strand displacement amplification (SDA), the cycling probe amplification reaction (CPR), branched DNA (bDNA) and other DNA and RNA polymerase mediated techniques are known. Examples of these and related techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990); WO 94/11383; Vooijs et al. (1993) *Am J. Hum. Genet.* 52: 586–597; *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Sooknanan and Malek (1995) *Bio/Technology* 13, 563–564; Walker et al. *Proc. Natl. Acad. Sci. USA* 89, 392–396), and Barringer et al. (1990) *Gene* 89, 117. Improved methods of cloning in vitro amplified nucleic acids are described in Wallace et al., U.S. Pat. No. 5,426,039.

Methods of producing polymers in vitro and in vivo, such as polyclonal and monoclonal antibodies are also known to those of skill in the art. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546.

Solid phase synthesis of polymers, including biological polymers is also known. See, e.g., Merrifield (1963) *J. Am. Chem. Soc.* 85: 2149–2154. Solid-phase synthesis techniques have also been provided for the synthesis of peptide sequences on, for example, a number of "pins." See e.g., Geysen et al. (1987) *J. Immun. Meth.* 102: 259–274 and Holmes et al (filed Jan. 17, 1995) Ser. No. 08/374,492. Other solid-phase techniques involve, for example, synthesis of various peptide sequences on cellulose disks supported in a column. See Frank and Doring (1988) *Tetrahedron* 44: 6031–6040. Still other solid-phase techniques are described in U.S. Pat. No. 4,728,502 (Hamill) and WO 90/00626 (Beattie).

Oligonucleotide synthesis is optionally performed on commercially available solid phase oligonucleotide synthesis machines (see, Needham-VanDevanter et al. (1984) *Nucleic Acids Res.* 12:6159–6168) or manually synthesized using the solid phase phosphoramidite triester method described by Beaucage et al. (Beaucage et al. (1981) *Tetrahedron Letts.* 22 (20): 1859–1862) prior to attachment on a solid substrate. Bead-based synthetic techniques are described in copending application U.S. Ser. No. 07/762,522 (filed Sep. 18, 1991); U.S. Ser. No. 07/946,239 (filed Sep. 16, 1992); U.S. Ser. No. 08/146,886 (filed Nov. 2, 1993); U.S. Ser. No. 07/876,792 (filed Apr. 29, 1992); PCT/US93/04145 (filed Apr. 28, 1993); and Holmes et al. (filed Jan. 17, 1995) U.S. Ser. No. 08/374,492. Finally, as described above, polymers are optionally synthesized using VLSIPS™ methods in arrays, or optionally cleaved from the array and then reattached to a solid substrate to form a second array.

Cleavable Linkers

Cleavable linking groups used in VLSIPS™ and other solid phase synthetic techniques are known. Typically, linking groups are used to attach polymers or labeled polymers during the organic synthesis of polymer arrays. In addition, in some embodiments, polymer arrays are used prior to cleavage from the arrays, typically in aqueous hybridization experiments. Thus, preferred linkers operate well under organic and aqueous conditions, but cleave readily under specific cleavage conditions. The linker is typically provided with a spacer having active cleavable sites. In the particular case of oligonucleotides, for example, the spacer is selected from a variety of molecules which can be used in organic environments associated with synthesis as well as aqueous environments, e.g., associated with nucleic acid binding studies. Examples of suitable spacers are polyethyleneglycols, dicarboxylic acids, polyamines and alkylenes, substituted with, for example, methoxy and ethoxy groups. Linking groups which facilitate polymer synthesis on solid supports and which provide other advantageous properties for biological assays are known. In some embodiments, the linker provides for a cleavable function by way of, for example, exposure to an acid or base.

Additionally, the linkers have an active site on the distal end, relative to the attachment of the linker to the solid substrate. The active sites are optionally protected during polymer synthesis using protecting groups. Among a wide variety of protecting groups which are useful are nitroveratryl (NVOC) α-methylnitroveratryl (Menvoc), allyloxycarbonyl (ALLOC), fluorenylmethoxycarbonyl (FMOC), α-methylnitro-piperonyloxycarbonyl (MeNPOC), —NH—FMOC groups, t-butyl esters, t-butyl ethers, and the like as described, e.g., by Holmes et al. (id). Various exemplary protecting groups are described in, for example, Atherton et al., (1989) *Solid Phase Peptide Synthesis*, IRL Press, and Greene, et al. (1991) *Protective Groups In Organic Chemistry*, 2nd Ed., John Wiley & Sons, New York, N.Y. The proper selection of protecting groups for a particular synthesis is governed by the overall methods employed in the synthesis. For example, in "light-directed" synthesis, discussed herein, the protecting groups are photolabile protecting groups such as NVOC, MeNPoc, and those described in co-pending Application PCT/U593/10162 (filed Oct. 22, 1993). See also, Holmes et al. (supra); Wang (1976) *J. Org. Chem.* 41: 3258; and Rich, et al. (1975) *J. Am. Chem. Soc.* 97: 1575–1579. In other methods, protecting groups are removed chemically, and include groups such as FMOC, di(p-methoxyphenyl)phenyl (DMT) and others known to those of skill in the art. See, Holmes et al. (supra).

Some of the linking groups are hydrophilic and provide a "wettable" surface which aids in synthesis of the polymers as well as in screening of the polymers for activity. Other linking groups are more hydrophobic. A variety of hydrophobic and hydrophilic cleavable linkers suitable for use in polymer array synthesis are described in the patents and applications relating to VLSIPS™ synthesis described supra.

The linker attaches to the solid substrate through a variety of chemical bonds. For example, the linker is optionally attached to the solid substrate using carbon—carbon bonds, for example via substrates having (poly)trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups.

The particular linking group is selected based upon, e.g., its hydrophilic/hydrophobic properties where presentation of an attached polymer in solution is desirable. Groups which are suitable for attachment to a linking group include amine, hydroxyl, thiol, carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

Labeling of Polymers

In preferred embodiments, the present invention proceeds by labeling polymers in arrays, which are then cleaved from the arrays and analyzed. A variety of labels are appropriate and known. A "label" comprises a moiety which is detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, haptens and proteins. In preferred embodiments, the label is detectable spectroscopically, i.e., is chromogenic. Suitable chromogens include molecules and compounds which absorb light in a distinctive range of wavelengths so that a color may be observed, or emit light when irradiated with radiation of a particular wavelength or wavelength range (e.g., a fluorescent label). In preferred embodiments, labels of the present invention have the structure A-B, where A is a detectable moiety, and B is a "linking" or "bridging" group which comprises one or more functional regions which allow the detectable moiety to be incorporated into a polymer, or attached to one end of the polymer, using chemistry similar to that used to connect monomers into the polymer. Examples of suitable bridging regions include alkyl and substituted alkyl carbon chains with 1–30 carbons, or more preferably 3–10 carbons, with functional groups such as oxygen and phosphate (i.e., when the polymer is an oligonucleotide) or amino and carboxyl (i.e., where the polymer is a peptide).

For example, in preferred embodiments where the label is a nucleic acid synthesis reagent to be incorporated into a nucleic acid, the bridging group has the structure

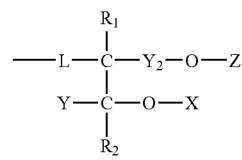

wherein

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation;

$R_1$ is selected from the group consisting of hydrogen, alkyl, and aryl;

$R_2$ is selected from the group consisting of hydrogen, alkyl, and aryl;

X is a nucleic acid integration element comprising a phosphorous atom;

Y is selected from the group consisting of hydrogen, alkyl, and aryl;

$Y_2$ is an alkyl chain; and

Z comprises a protecting group.

In more preferred embodiments in which the label is a nucleic acid synthesis reagent to be incorporated into a nucleic acid, the bridging group has the structure

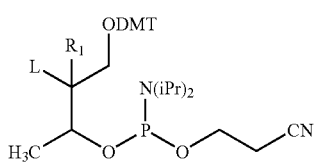

wherein

L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation. Typically L is joined to a detectable moiety such as a fluorophore. $R_1$ is selected from the group consisting of hydrogen, alkyl, and aryl, and more preferably is selected from the group consisting of hydrogen or methyl.

In preferred embodiments, the nucleic acid synthesis reagent (A-B, i.e., the detectable moiety and the integration or bridging element) has the structure

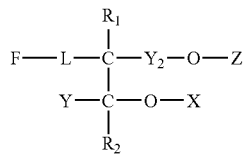

wherein L is an alkyl linking group from 1 to 30 carbons in length, wherein one or more carbon is optionally replaced or substituted with a heteroatom selected from the group consisting of N, S, O and P, and is optionally part of a ring system, and wherein the alkyl linking chain optionally includes one or more site of unsaturation; $R_1$ is selected from the group consisting of hydrogen, alkyl, and aryl; $R_2$ is selected from the group consisting of hydrogen, alkyl, and aryl; X is a nucleic acid integration element comprising a phosphorous atom; Y is selected from the group consisting of hydrogen, alkyl, or aryl; $Y_2$ is an alkyl chain from 1 to 30 carbons in length; Z comprises a protecting group; and F comprises a fluorescent group.

In a still more preferred embodiment, the nucleic acid synthesis reagent has the structure wherein $R_1$ is selected from the group consisting of alkyl, aryl, and hydrogen; $R_2$ is selected from the group consisting of hydrogen, alkyl and aryl; and FL is a fluorescent moiety. An example of such a nucleic acid synthesis reagent label is the isomeric nucleic acid synthesis reagent with the structure In particularly preferred embodiments, the label is mono-isomeric (or more simply "isomeric"), i.e., when incorporated into a polymer does not provide multiple isomeric species, e.g., as detected by HPLC. The Examples below describe a novel fluorescent label (fluorescein phosphoramidite 7, See below) which is isomeric. A variety of suitable labels are constructed by converting existing detectable groups, including quinoline, triarylmethane, acridine, alizarine, phthaleins, azo labels, anthraquinoid tags, cyanine, phenazathionium, and phenazoxonium into mono-isomeric forms. In one set of preferred embodiments (see, e.g., Example 1, below), a mono-isomeric detectable moiety is connected to a mono-isomeric bridging region and appropriate functional groups which allow for incorporation of the label into a polymer by the same chemistry as that used to connect the monomers of a polymer. For instance, amino acids are optionally used to form the linking regions of labels, with suitable groups being added for incorporation of the label into the polymer (e.g., hydroxy and phosphate groups are attached to the linking region for incorporation into oligonucleotides (see, Example 1 below), or attached to amino and carboxy groups for incorporation into peptides). Amino acid linking regions are preferred because of the ready availability of mono-isomeric amino acids (e.g., D or L isomers) and the presence of reactive functional groups.

A variety of fluorescent groups are suitable, or are rendered suitable by converting the group to a mono-isomeric form, either alone or in conjunction with quencher molecules. Suitable fluorescent labels are typically characterized by one or more of the following: high sensitivity, high stability, low background, low environmental sensitivity and high specificity in labeling. As described herein, suitable labels are also preferably mono-isomeric.

Fluorescent moieties, which are incorporated into the labels of the invention, or are converted into mono-isomeric forms and then incorporated into the present invention, are generally are known, including 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridiium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanatostilbene2,2'-disulfonic acid; pyrene-3-sulfonic acid; 2-toluidinonaphthalene-6sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; NN,N'-dihexyl oxacarbocyanine; merocyanine, 4-(3'pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis(2-(4-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3chromenyl)maleimide; N-(p-(2-benzimidazolyl)-phenyl)maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound label may differ from the unbound label. Therefore, when referring to the various wavelength ranges and characteristics of the labels, it is intended to indicate the labels as employed and not the label which is unconjugated and characterized in an arbitrary solvent.

Fluorescent labels are generally preferred, in part because by irradiating a fluorescent label with light, one can obtain a plurality of emissions. Thus, a single label can provide for a plurality of measurable events. Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. The most popular compound is luminol, which is the 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Other useful chemiluminescent compounds are also known and available, including -N-alkyl acridinum esters (basic $H_2O_2$) and dioxetanes. Alternatively, luciferins may be used in conjunction with luciferase or lucigenins to provide bioluminescence.

Isomerism

If a molecule is not superimposable on its mirror image, it is chiral (optically active). If a molecule can be superimposed on itself, it is achiral (optically inactive). Mirror image molecules are referred to as enantiomers. A molecule can have one or more chiral center, typically carbon, nitrogen or phosphorous atoms with unique substituents (i.e., none of the substituents on a chiral atom can be the same as another substituent on the same atom). Molecules in compounds with more than one chiral center are referred to as diastereomers. The properties of diastereomers are typically similar, but not identical. For instance, diastereomers typically interact with other compounds in different ways (particularly chiral compounds, and particularly at chiral centers within compounds), and migrate through size or charge matrices at different rates. One effect of the difference between properties of diastereomers is that they often migrate through HPLC columns at different rates. Thus, the use of diastereomer labels in the present invention makes resolution by size of polymers after cleavage from a solid substrate more difficult using techniques such as column chromatography, HPLC, capillary electrophoresis, or gel electrophoresis.

Accordingly, a preferred embodiment of the present invention utilizes a single optical isomer of all the possible diastereomers of a particular molecule as a label. Methods of purifying diastereomers, and methods of purifying enantiomers used to make diastereomers (i.e., "asymmetric synthesis") are known in the art. March (1992) *Advanced Organic Chemistry: Reactions, Mechanisms and Structure* Fourth Edition, John Wiley and Sons and the references therein, particularly chapter 4, and Lide (ed) *CRC Handbook of Chemistry and Physics* 75th edition and the references therein provide a general guide for the purification of stereoisomers. Briefly, a pair of enantiomers can be separated by reaction with a stereoselective reagent, reactions in the presence of circularly polarized light, or, most commonly, by conversion to diastereomers and subsequent purification. Typically, enatiomers are converted to diastereomers by reaction with an optically active acid or base to form a diastereomeric salt. The diastereomeric salt is crystalized into distinct diastereomers, and separated by distillation, gas chromatography, HPLC, or preparative liquid chromatography as appropriate. Similarly, diasteromers in general are separated by distillation, gas chromatography, HPLC or preparative liquid chromatography.

Post-Synthetic Labeling of Polymers

In one preferred class of embodiments, the present invention provides for post-synthetic labelling of polymer arrays. As described herein, the labeling of polymers in arrays is optionally performed by adding the label at the end of the polymer proximal to the surface to which the polymers of the array are attached, to the end distal to the surface, or as a monomeric building block of the polymer at any position within the polymer. In certain applications, it will be preferable to label the polymers of the array at the end of the array distal to the attachment surface, i.e., after the synthesis of the polymers in the array. This is especially useful where the chemistry used for synthesizing the polymer is not compatible with the addition of monomers of the polymer to the labeling reagent.

Figure 2:
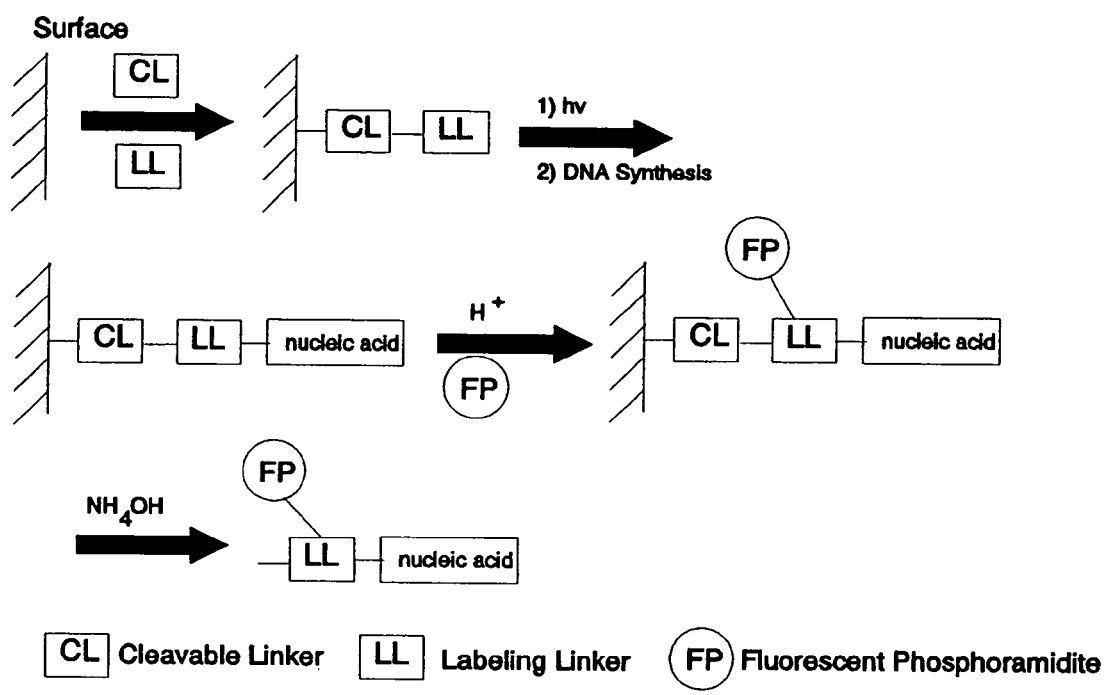
FIG. 2 provides a post-synthetic labeling scheme for oligonucleotide probe arrays.

In one preferred class of embodiments, a second method for adding the detectable moiety after the polymer is synthesized is provided. In this method, a labeling linker is incorporated into the polymer at a chosen site, and a detectable moiety (e.g., fluorophore or chromogenic agent) is added to the polymer by attachment to the labeling linker. FIG. 2 shows one application of this strategy.

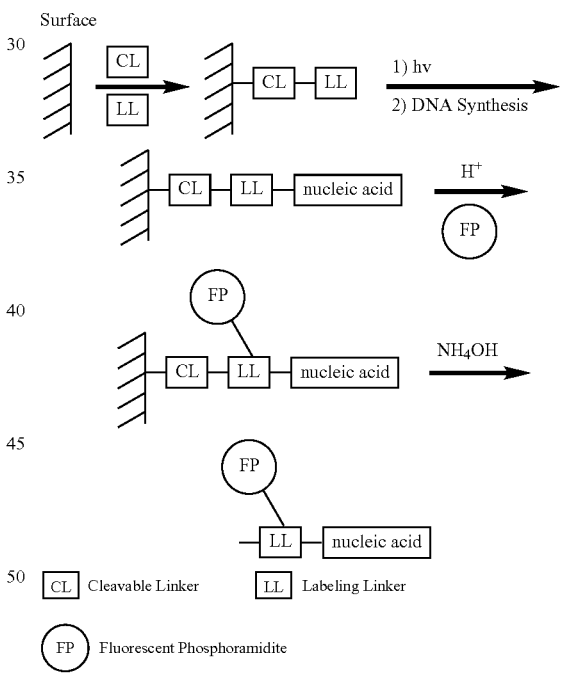

In this preferred embodiment, a labeling linker is attached to a cleavable linker bound to a solid substrate. The labeling linker has a site with appropriate chemistry to link with the cleavable linker, a second site with appropriate chemistry for adding monomers for polymer elongation, and a third site with appropriate chemistry for linking with the detectable moiety. After polymer synthesis, the detectable fluorophore is added to the site within the labeling linker with the appropriate chemistry for binding the fluorophore.

In this preferred embodiment, the site in the labeling linker which accepts the fluorophore is protected by an appropriate protecting group such as DMT until the fluorophore is added. The protecting group is then removed, for example by reduction, and the fluorophore is added, for example by a condensation reaction. The polymer is then optionally cleaved from the array by cleaving the cleavable linker, and then analyzed by the methods described herein (HPLC, capillary gel electrophoresis, etc.).

For clarity, FIG. 2 is directed to a post-synthetic labeling scheme for oligonucleotide arrays; however, one of skill will readily appreciate that the same strategy (i.e., the use of a labeling linker with sites for polymer elongation, attachment to a surface or cleavable moiety, and for binding a fluorophore or other detectable moiety), is also useful for in the synthesis and detection of polypeptide arrays, as well as other polymer arrays. One of skill will also appreciate that the labeling linker is optionally incorporated into the polymer chain, or located at the end of the polymer distal to the synthesis surface, depending on the desired application.

The labeling linker optionally has additional sites. For example, the labeling linker can incorporate a cleavable functionality, i.e., the labeling linker can be constructed to incorporate a cleavable site to allow separation from an array substrate. The labeling linkers can also have more than one site for the attachment of detectable moieties.

In one preferred embodiment, the labeling linker has the structure shown below.

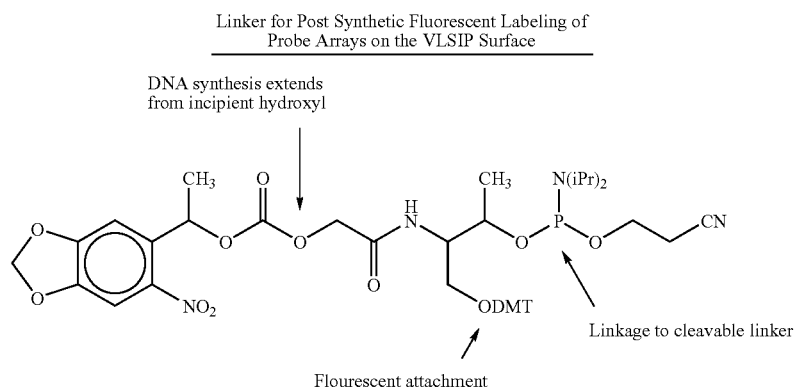

A synthesis scheme for synthesizing the labeling linker is provided below.

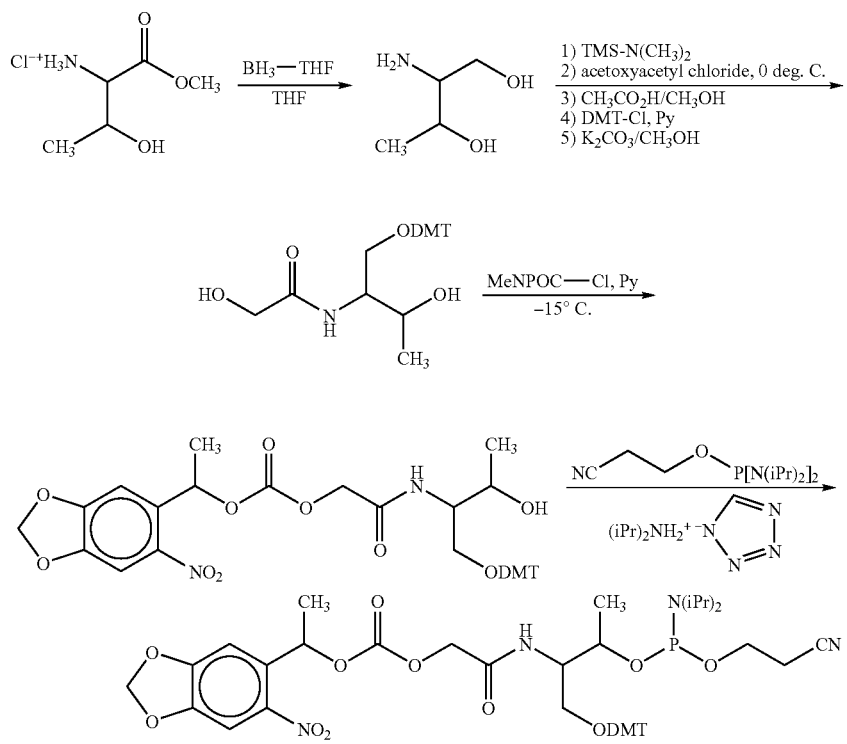

Another exemplar linker for post-synthetic labeling of oligonucleotide arrays has the chemical structure shown below.
Linker for Post Synthetic Fluorescent Labeling of Probe Arrays
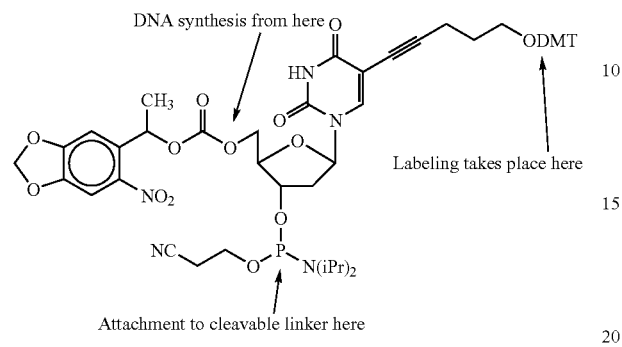
A synthetic scheme for the post-synthetic labeling linker is provided below.
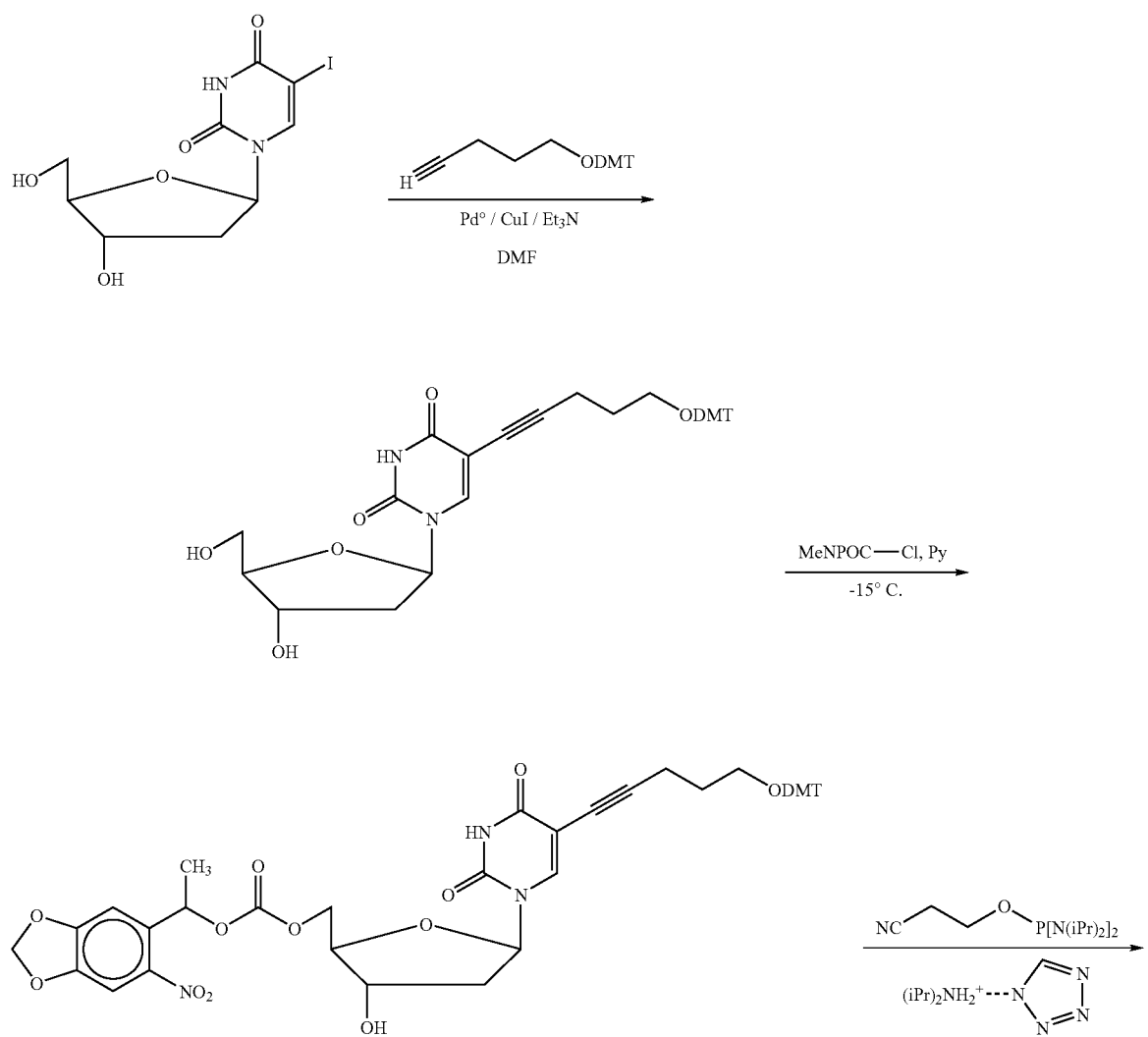

-continued

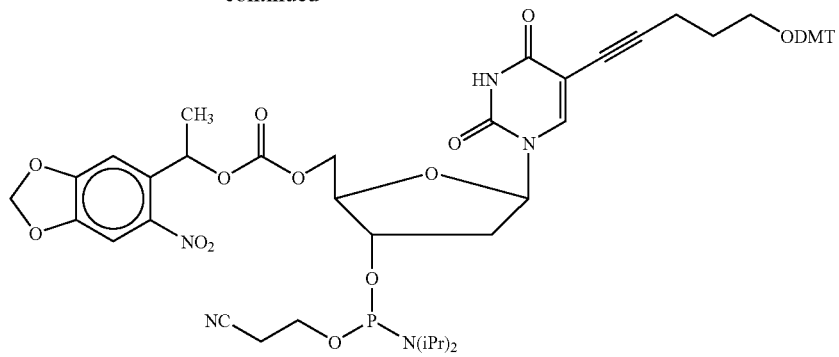

Purification of Polymers Cleaved from Arrays.

Polymers cleaved from VLSIPS arrays are purified according to a variety of known techniques, including, but not limited to, gel electrophoresis, column chromatography, immunopurification, precipitation, crystallization, dialysis, filtration, high pressure liquid chromatography (HPLC), flash chromatography, paper chromatography and affinity chromatography. See, e.g., Sambrook, supra; Ausubel, supra; R. Scopes, *Protein Purification*, Springer-Verlag, N.Y. (1982); Hochuli (1989) *Chemische Industrie* 12:69–70; Hochuli (1990) "*Purification of recombinant proteins with Metal Chelate Absorbent*" in Setlow (ed.) *Genetic Engineering, Principle and Methods* 12:87–98, Plenum Press, N.Y.; Crowe, et al. (1992) *QIAexpress: The High Level Expression &Protein Purification System* QUIAGEN, Inc., Chatsworth, Calif.; Maniatis, et al. (1982) *Molecular Cloning, A Laboratory Manual* Cold Spring Harbor Laboratory, Cold Spring Harbor Press; Sambrook (supra); Ausubel (supra); Innis (supra); Harlow and Lane (supra); Deutscher (1990) "*Guide to Protein Purification*" in *Methods in Enzymology* vol. 182, and other volumes in the *Methods in Enzymology* series; and manufacturer's literature on use of protein purification products, e.g., Pharmacia, Piscataway, N.J., and Bio-Rad, Richmond, Calif., In preferred embodiments, the polymer cleaved from a VLSIPS™ array is labeled with a detectable label, facilitating purification. HPLC is a preferred method of purifying polymers cleaved from a VLSIPS array. HPLC typically allows for the simultaneous detection and quantitation of a label as it exits an HPLC column, e.g., by monitoring the efflux from an HPLC column with a photomultiplier tube, providing a method of rapidly determining the quantity and size of polymers cleaved from an array. However, other methods such as capillary gel electrophoresis and standard column chromatography provide similar information, particularly when coupled with a photomultiplier or scintillation counter.

Once a polymer is purified, it is optionally analyzed further, for example, to determine the precise sequence of the monomers which comprise the polymer. Many appropriate techniques are known, including nuclear magnetic resonance spectroscopy (NMR), chemical sequencing (e.g., the Maxam-Gilbert chemical sequencing reaction used to sequence nucleic acids), enzymatic sequencing (e.g., cloning and dideoxy sequencing used to sequence nucleic acids) crystallography, circular diachroism, stopped flow spectroscopy etc. Where the polymer is a nucleic acid, it is also possible to clone the nucleic acid using standard techniques (see, e.g., Sambrook, supra).

EXAMPLES

The following examples are provided by way of illustration only and not by way of limitation. One of skill will recognize a variety of parameters which can be changed or modified to yield essentially similar results.

Materials and Nomenclature 5-carboxyfluorescein was obtained from Applied Biosystems, Foster City Calif.

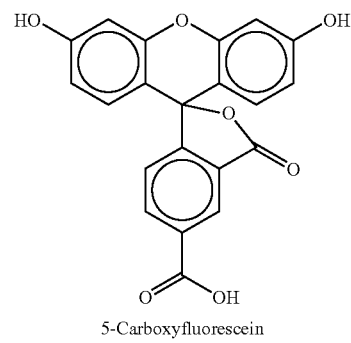

5-Carboxyfluorescein

Pivalic anhydride, pyridine, dicyclohexylcarbodiimide (DCC), N-hydroxysuccinimide (NHS), borane-tetrahydrofuran complex (BH$_3$.THF), acetic acid, methanol, 4,4'-dimethoxytrityl chloride, piperidine, dimethylformamide (DMF), triethylamine (Et$_3$N), 2-cyanoethyl N,N,N',N'-tetraisopropyl-phosphoramidite, and diisopropylammonium tetrazolide were all obtained from The Aldrich Chemical Company, Milwaukee Wis.

L-threonine methyl ester hydrochloride and N-Fmoc-γ-aminobutyric acid were obtained from Bachem, Calif. N-Fmoc-γ-aminobutyryl pivolate was synthesized from N-Fmoc-γ-aminobutyric acid and pivoloyl chloride.

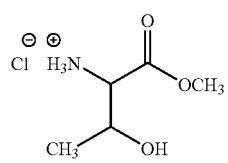

L-threonine methyl ester, hydrochloride

-continued

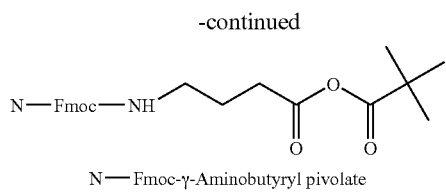

N—Fmoc-γ-Aminobutyryl pivolate

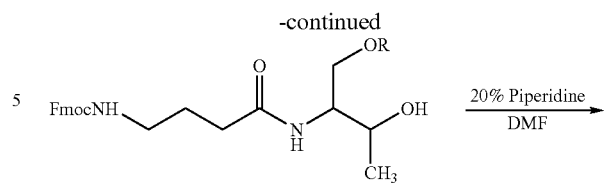

2 R = H
3 R = DMT

Example 1

Procedure for the Synthesis of a Novel Fluorescent Phosphoramidite (Fluorescein Phosphoramidite 7)

For the example below, see also FIG. 1 which provides a reaction scheme for the synthesis of fluorescein phosphoramidite 7. The fluorescent phosphoramidite was used in conjunction with a cleavable linker at the 3' end of the oligonucleotide polymer for synthesizing an oligonucleotide array on a chip using the VLSIPS™ light-directed synthesis procedure. The oligonucleotides were then cleaved from the array at the cleavable linker and analyzed by HPLC. The general strategy for synthesis is depicted below (see also, FIG. 1).

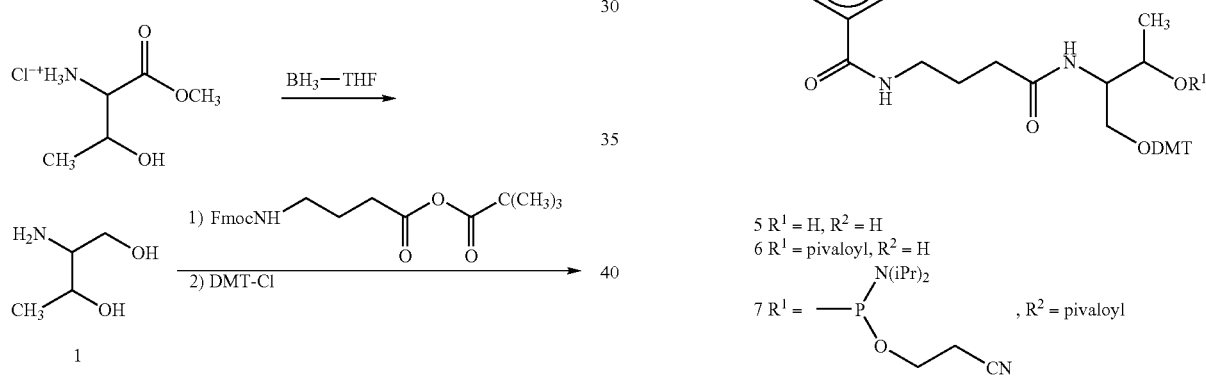

5 R¹ = H, R² = H
6 R¹ = pivaloyl, R² = H
7 R¹ = $\begin{array}{c}\text{N(iPr)}_2\\|\\-\text{P}\\|\\\text{O}\diagdown\diagdown\text{CN}\end{array}$ , R² = pivaloyl

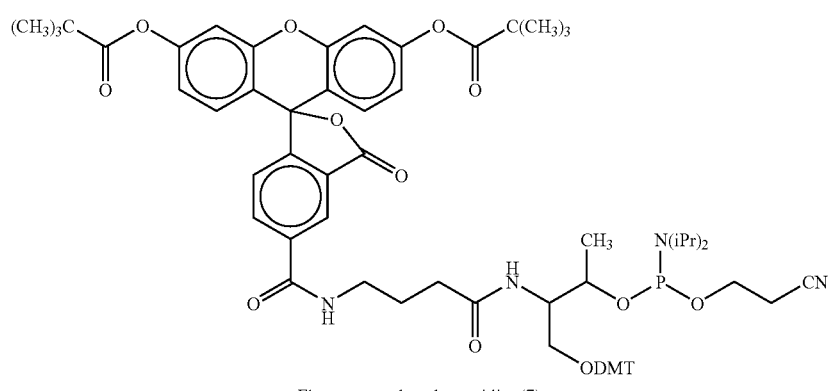

Fluorescent phosphoramidite (7)

is synthesized from a fluoresceinated linker (6),

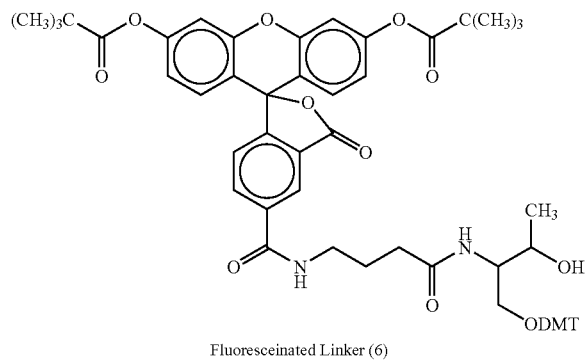

Fluoresceinated Linker (6)

which is synthesized from two units, 5-carboxyfluorescein N-hydroxysuccinimidyl ester (5) and (2S,3R)-4-aminobutaneamido-1,3-butanediol trityl ether (6),

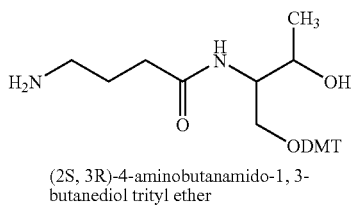

(2S, 3R)-4-aminobutanamido-1,3-butanediol trityl ether

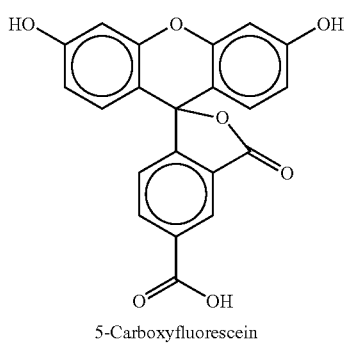

5-Carboxyfluorescein each of which exists as a single isomer (See also FIG. 1). This insures that, contrary to existing systems used as an oligonucleotide label, the attachment of the fluorescent phosphoramidite 7 results in an oligonucleotide with only one isomer. This allows oligonucleotides with the fluorescent label 7 to be fractionated by size (e.g., by HPLC as shown below) without the complication of isomeric mixtures of single size classes.

(2S,3R)-2-amino-1,3-butanediol (1)

To 15 g (88.4 mmol, 1 eq) of L-threonine methyl ester hydrochloride in 100 mL of dry THF at 0° C. under argon was added, dropwise over 1 hr, 265.3 mL (265.3 mmol, 3 eq) of borane-THF (1 M). The ice bath was removed and the reaction was stirred at room temperature overnight (18 hr). The solution was cooled to 0° C. and quenched slowly with 180 mL of 10% acetic acid in methanol. The solution was then evaporated to a brown viscous oil and the oil co-evaporated three times with 100 mL of methanol. The crude material was purified by flash chromatography on silica gel using a step gradient of 1% to 5% conc. Ammonium hydroxide in methanol/dichloromethane 3:7 to afford 7.5 g (81%) of (2S,3R)-2-amino-1,3-butanediol as a viscous oil. This material was dissolved in 50 mL of dry DMF and precipitated with hexanes in the cold to give 1 as a white solid.

(2S-3R)-2-[4'-N-[fluoren-9-ylmethoxy)-carbonyl]-4'-aminobutanamido]-1,3-butaned iol (2)

To 5 g (15.4 mmol, 1 eq) of N-Fmoc-4-aminobutyric acid and 8 mL (46.1 mmol, 3 eq) of dry diisopropylethylamine in 60 mL of dry THF at 0° C. under argon was added 2 mL (16.1 mmol, 1.05 eq) of pivaloyl chloride. The solution was stirred for 1 hr at 0° C. and then 1.8 g (16.9 mmol, 1.1 eq) of 1 was added in 8 mL of dry DMF. The solution was allowed to warm to room temperature and the solvent removed under vacuum. The oil was dissolved in 100 mL of ethyl acetate and washed with 100 mL of sat. aq. NaHCO$_3$ and 100 mL of brine and dried over anhydrous Na$_2$SO$_4$. Filtration and solvent removal gave 7 g of an oil. The crude product was purified by flash chromatography on silica gel using ethyl acetate/hexanes/1% triethylamine as eluent to afford 3.4 g (53%) of 2 as a yellow foam.

Protection of the Primary Hydroxyl with DMTCl to Give 3

To 3.4 g (8.2 mmol, 1 eq) of 2 in 30 mL of dry pyridine under argon at ambient temperature was added 3.1 g (9.1 mmol, 1.1 eq) of 4,-4'-dimethoxytrityl chloride. The reaction was stirred for 18 hr and then the solvent removed under vacuum. The oil was taken up in 50 mL of ethyl acetate and washed twice with 50 mL of saturated aqueous NaHCO$_3$ and 50 mL of brine and dried over anhydrous Na$_2$SO$_4$. Filtration and removal of solvent gave about 7 g of an orange oil. The crude product was purified by flash chromatography on silica gel using ethyl acetate/hexanes 3:2 and 1% triethylamine as eluent to afford 4.7 g (80%) of 3 as a white foam.

Deprotection of the Fmoc Group to Give 4

The FMOC group was removed by treatment of 4.7 g (6.6 mmol) of 3 with 50 mL of 20% piperidine in DMF for 2 hr at ambient temperature. The solvent was removed under vacuum to give a white solid. The solid was dissolved in 200 mL of ethyl acetate and washed twice with 100 mL of saturated aqueous NaHCO$_3$ and 100 mL of brine and dried over anhydrous Na$_2$SO$_4$. Filtration and evaporation of the solvent gave a white solid which was purified through a plug of silica gel using ethyl acetate/1% triethylamine to remove the fulvene followed by elution with 60% methanol/ethyl acetate/1% triethylamine to afford 2.5 g (89%) of 4 as a white foam.

Reaction of 5-Carboxyfluorescein N-hydroxysuccinimide with 4 to Give 5

4 g (10.6 mmol, 1 eq) of 5-carboxyfluorescein was co-evaporated twice under vacuum with 30 mL of dry pyridine and the mixed with 1.2 g (10.6 mmol, 1 eq) of N-hydroxysuccinimide and 2.3 g (10.6 mmol, 1 eq) of dicyclohexylcarbodiimide in 100 mL of dry THF under argon. The reaction was stirred at ambient temperature for 18 hr and then filtered to remove the insoluble urea. The solvent was removed under vacuum to afford 5 g of an orange solid. To the crude NHS-ester in 50 mL of 10% pyridine in dichloromethane was added amine 4 in 20 mL of dichloromethane under argon. The reaction was stirred overnight (18 hr) at ambient temperature. The reaction was poured into 100 mL of brine and the aqueous layer was extracted twice with 100 mL of dichloromethane/isopropyl alcohol 1:1. the organic fractions were combined and dried over anhydrous $Na_2SO_4$. Filtration and removal of solvent gave an orange solid which was purified by flash chromatography on silica gel using a stepwise gradient of 5% to 30% methanol/dichloromethane to afford 7.5 g (83%) of 5 as a yellow solid.

Protection of 5 as the Pivaloate 6

To 7.5 g (8.2 mmol, 1 eq) of 5 in 30 mL of dry dichloromethane under argon at ambient temperature was added 12.3 mL (16.4 mmol, 2 eq) of triethylamine and 0.2 g (1.6 mmol, 0.2 eq) of dimethylaminopyridine followed by 6.4 mL (16.4 mmol, 2 eq) of pivaloic anhydride. The reaction was stirred for 20 hr and washed twice with 100 mL of dilute aqueous $NaHCO_3$ (1/10 from saturation) and 100 mL of brine dried over anhydrous $Na_2SO_4$. Filtration and evaporation of the solvent under vacuum gave a pale yellow foam which was purified by flash chromatography on silica gel using a methanol/dichloromethane/ethyl acetate mixture to afford 5.5 g (66%) of 6 as a white solid.

Phosphitylation of 6

The procedure of Barone, et al (See, Barone, et. al., (1984) *Nucleic Acids Research,* 12:4051 and Reynolds, et. al. (1992) *Bioconjugate Chemistry,* 3:366) was followed to form the cyanoethyl phosphoramidite 7 in 80% yield after chromatography on silica gel using 30% hexanesu/ethyl acetate as eluent.

Example 2

Analysis of Probe Arrays

This Example describes the quantitative analysis of an array synthesized by the VLSIPS™ method (See, (1994) *Proc. Natl. Acad. Sci. USA,* 91: 5022), by cleavage of the array from the surface of a test pool of oligonucleotide probes. The probes were labeled at the 3'-end with a fluorophore (using the fluorescein phosphoramidite 7, see supra), which were fractionated by HPLC. The information obtained from this assay includes overall yield of full-length probe (P) (pmol), density of full-length probe (D) (in pmol/$cm^2$), coupling efficiency for a given nucleoside phosphoramidite used in the synthesis of the probe array, and density of available sites for reaction on the substrate (in this case a silane surface) Ds (pmol/$cm^2$).

Synthesis of Fluorescein-Labeled Deoxyoligonucleotide Calibration Standard ($T_{16}$)

Calibration sequences were synthesized on a 1 μmole scale using standard DMT-protected, cyanoethyl nucleoside phosphoramidite reagents at 100 mM and the fluorescein phosphoramidite 7, and SL phosphoramidites at 50 mM. The sequence of the calibration standard had the following construction:

CPG-T-SL-FL-3'TTTTTTTTTTTTTTTT5'-DMT

Where CPG is a controlled pore glass substrate, SL is the commercially available sulfone linker phosoramidite linker, and FL is fluorescein phosphoramidite 7.

The DMT-on poly-16mer was cleaved automatically from the CPG support on the synthesizer with 2 mL of conc. $NH_4OH$ into the collection vial containing 50 mL of 1 M NaOH (final concentration of NaOH is 25 mM), and allowed to stand in the dark at room temperature for 15 hr. The solution volume was reduced to about 0.5 mL in a speed-vac. The concentration of the oligonucleotide in $A_{495}$ units (au) per mL was determined by dilution of the crude solution to obtain an absorbance reading between 0.1 au and 1 au/mL. The solution was stored at −20° C. in the dark.

HPLC Purification of Calibration Oligonucleotide

The sample was microfuged (14,000 rpm) for 5 min to remove particulate matter, and then analyzed in small aliquots (0.25 au) by HPLC on a PRP-1 reverse-phase column at a flow rate of 2 mL/min, using 0–60% B linear gradient over 45 min ($R_t$=28 min) where 1× TEAA pH7=buffer A, and $CH_3CN$=buffer B with detection performed at 260/495 nm absorbance.

The remaining crude oligo was purified under the same conditions, except that detection was at 290/510 nm and 1 mL fractions were collected in 13×100 mm glass culture tubes across the main peak. The fractions spanning the peak were pooled and evaporated to dryness in a speed-vac. The residue was suspended in 1 mL of 80% acetic acid in an eppendorf tube and allowed to stand for 1 hr at room temperature. The solution was evaporated to dryness in a speed-vac and the residue suspended in 350 μL of $sdiH_2O$. The sample was then microfuged (14,000 rpm) for 5 min to pellet any particulate material.

The sample was then purified by HPLC on a tentacle ion-exchange column in a similar fashion as above at a flow rate of 1 mL/min and a 0–100% B linear gradient over 40 min $R_t$ (analytical)=17.4 min and $R_t$ (preparative) =13.5–17.5 min (broad peak) where 0.25× buffer A=buffer A and 1× buffer B=buffer B as described above. Detection was carried out at 260/495 nm absorbance for the analytical peak and 290/510 nm absorbance for the preparative peak. Fractions were collected in 0.5 ml fractions in 13×100 mm glass culture tubes.

Fractions (40–50 μL) were analyzed on a dionex ion-exchange column with a flow rate of 1 mL/min, a 0–100% B linear gradient over 30 min ($R_t$=24.3 min), using 0.25× buffer A and 1× buffer B. Fractions were monitored at 260/495 nm absorbance The purest fractions (>93% pure) were pooled, neutralized with acetic acid (tested against litmus paper) and evaporated to dryness in a speed-vac. The residue was suspended in 1 mL of $sdiH_2O$ and desalted on a sep-pak plus C18 cartridge using the manufacturer's recommended procedure, except that the oligonucleotide was eluted with 80% aqueous acetonitrile. The combined fractions were evaporated to dryness and suspended in 200 μL of $sdiH_2O$. Two aliquots of the pool were again tested by dionex chromatography for final purity (93%), first by detecting one aliquot at 260/495 nm absorbance and second by detecting the second aliquot at 520 nm fluorescence emission (495 nm excitation). The combined fractions were then pooled at −20° C. in the dark.

Chip Synthesis and Cleavage

The test probe sequence (below) was synthesized on a glass VLSIPS™ substrate employing standard VLSIPS™ techniques using DMT nucleodside phophoramidites.

SURFACE-silane-Peg-SL-FL-3'-TTTTTTTTTTTTTTTT5'-OH

After synthesis, the chip was placed in a 15 mL amber-glass bottle. 2 mL of fresh, cold conc. NH$_4$OH (stored at −20° C.) was added, and the bottle sealed tightly with a screw-cap and allowed to stand at room temperature for a minimum of 15 hrs. The solution was transferred with a pipetman to a 6 mL glass culture tube and the bottle/chip rinsed twice with 1 mL of sdiH$_2$O and the rinse portions were added to the tube. The solution was evaporated to dryness in a speed-vac at medium heat and the residue suspended in 1 mL of sdiH$_2$O (2×0.5 mL rinses).

The above test samples and the calibration samples were spun in a microfuge (14,000 rpm) for 5 min. 1 mL of the calibration set and test samples were added to injection vials and analyzed in triplicate on a dionex HPLC ion-exchange column with a flow rate=1 mL/min, 0–100% B linear gradient over 30 min, 0.25× buffer A and 1× buffer B. Detection of the test and reference (calibration) oligos was performed at 520 nm fluorescence (495 nm excitation), with the photomultiplier tube (PMT) sensitivity set to medium and injection volume=100 μL (full-loop mode).

Figure 3:
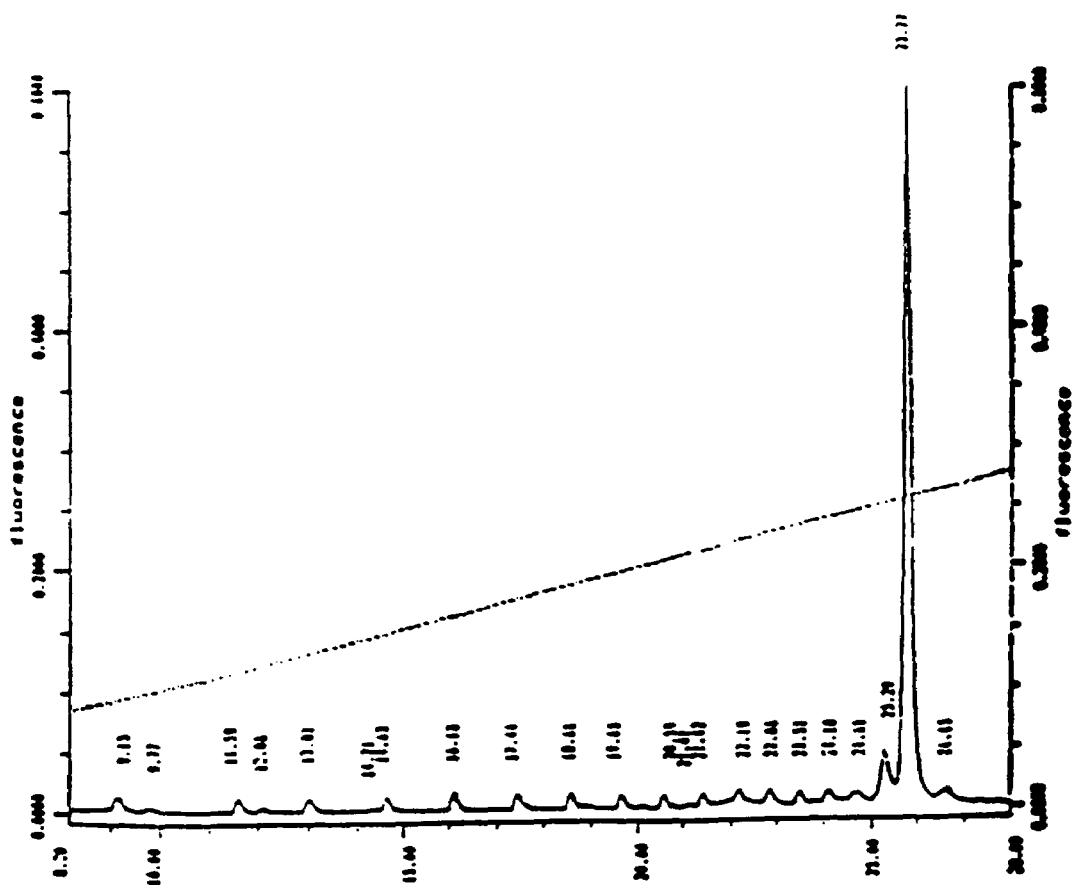
FIG. 3 provides a chromatogram of a fluorescein-labeled $T_{16}$ homopolymer.

General Features of the HPLC Chromatogram of the Homopolymer T16 Synthesized Using DMT Chemistry FIG. 3 shows a typical HPLC chromatogram of a fluorescein-labeled T$_{16}$ homopolymer. The predominant peak at 25.77 min. corresponds to the full length 16-mer with a number of smaller truncated species that trail.

Although the foregoing invention has been described in some detail by way of illustration and example for purposes of clarity of understanding, modifications can be made thereto without departing from the spirit or scope of the appended claims.

All publications and patent applications cited in this specification are herein incorporated by reference for all purposes as if each individual publication or patent application were specifically and individually indicated to be incorporated by reference in its entirety for all purposes.

What is claimed is:

1. A method of monitoring polymer array synthesis on a solid substrate comprising:
   (i) synthesizing a preselected array of diverse biological polymers connected to a solid substrate, whereby the diverse biological polymers occupy different regions of the substrate and are spatially defined on the solid substrate on which the preselected array is synthesized, and wherein the diverse biological polymers comprise nucleotides, nucleosides, phosphoramidites, carbohydrates or natural or synthetic amino acids;
   (ii) cleaving the diverse biological polymers from the solid substrate thereby creating a mixture of diverse unbound biological polymers; and
   (iii) predicting a quantity of diverse biological polymers formed and comparing a measurement of quantity of diverse cleaved biological polymers from the array with the predicted quantity of diverse biological polymers formed as an indicator of the efficiency of the synthesis procedure, thereby determining the efficiency of the synthesis procedure.

2. The method of claim 1, wherein each of the polymers further comprises a label, thereby forming labeled polymers.

3. The method of claim 2, wherein each of the labeled polymers comprises a single isomeric label.

4. The method of claim 2, wherein the labeled unbound polymers are heterogeneous by number of monomeric units, and wherein the method further comprises separating the labeled unbound polymers by number of monomeric units.

5. The method of claim 2, wherein the labeled unbound polymers are heterogeneous by number of monomeric units, and wherein the method further comprises separating the labeled unbound polymers by charge using ion exchange chromatography.

6. The method of claim 2, wherein each of the labeled unbound polymers are heterogeneous by number of monomeric units, and wherein the method further comprises separating the labeled unbound polymers by number of monomeric units using capillary gel electrophoresis.

7. The method of claim 5, wherein the ion exchange chromatography is performed by HPLC.

8. The method of claim 5, wherein the ion exchange chromatography is performed by HPLC, and wherein the labeled unbound polymers are detected as they exit an ion exchange column.

9. The method of claim 1, wherein the polymer is an oligonucleotide.

10. A method for measuring the effect of altering a polymer array synthesis protocol, comprising:
    (i) synthesizing a preselected array of diverse biological polymers occupying different regions on a solid support by a first synthesis protocol, wherein the diverse biological polymers are spatially defined on the solid support on which the preselected array is synthesized, thereby creating a reference array of biological polymers, wherein the diverse biological polymers comprise nucleotides, nucleosides, phosphoramidites, carbohydrates or natural or synthetic amino acids;
    (ii) synthesizing a preselected array of diverse biological polymers occupying different regions on a solid support synthesized by a second synthesis protocol, wherein the diverse biological polymers are spatially defined on the solid support on which the preselected array is synthesized, and wherein the second synthesis protocol is different than the first synthesis protocol, thereby creating a test array of biological polymers; wherein biological polymers of the test array are preselected to be the same as preselected biological polymers of the reference array;
    (iii) cleaving separately the reference array of biological polymers and the test array of biological polymers, thereby creating a mixture of diverse cleaved biological polymers from the reference array and a mixture of diverse cleaved biological polymers from the test array;
    (iv) comparing a measurement of presence of diverse cleaved biological polymers from the test array as an indicator of the efficiency of the second synthesis procedure with a measurement of presence of diverse cleaved biological polymers from the reference array as an indicator of the efficiency of the first synthesis procedure, thereby determining whether a difference between the first and second synthesis procedure affects the efficiency of the second synthesis procedure.

11. The method of claim 10, wherein the test and reference polymers are oligonucleotides.

12. The method of claim 10, wherein the first synthesis protocol differs from the second synthesis protocol by a single variation.

13. The method of claim 10, wherein the reference polymers and the test polymers are attached to the solid substrate by a cleavable linker.

14. The method of claim 10, wherein the test and reference polymers comprise a detectable label.

15. The method of claim 14, wherein the label is a single isomeric label.

16. The method of claim 2, wherein the labeled polymers comprise a label comprising a fluorescent moiety.

17. The method of claim 14, wherein the detectable label comprises a fluorescent moiety.

18. A method of monitoring polymer array synthesis on a solid substrate comprising:
(i) synthesizing a preselected array of diverse polymers on a solid substrate, whereby the diverse polymers occupy different regions of the solid substrate and are spatially defined on the solid substrate on which the preselected array is synthesized;
(ii) cleaving the diverse polymers from the solid substrate thereby creating a mixture of diverse unbound polymers; and
(iii) predicting a quantity of diverse polymers formed and comparing a measurement of quantity of diverse cleaved polymers from the array with the predicted quantity of diverse polymers formed as an indicator of the efficiency of the synthesis procedure, thereby determining the efficiency of the synthesis procedure.

19. The method of claim 18, wherein each of the polymers further comprises a label, thereby forming labeled polymers.

20. The method of claim 19, wherein the labeled polymers comprise a label comprising a fluorescent moiety.

21. The method of claim 19, wherein each of the labeled polymers comprises a single isomeric label.

22. The method of claim 19, wherein the labeled unbound polymers are heterogeneous by number of monomeric units, and wherein the method further comprises separating the labeled unbound polymers by number of monomeric units.

23. The method of claim 19, wherein the labeled unbound polymers are heterogeneous by number of monomeric units, and wherein the method further comprises separating the labeled unbound polymers by charge using ion exchange chromatography.

24. The method of claim 19, wherein each of the labeled unbound polymers is heterogeneous by number of monomeric units, and wherein the method further comprises separating the labeled unbound polymers by number of monomeric units using capillary gel electrophoresis.

25. The method of claim 23, wherein the ion exchange chromatography is performed by HPLC.

26. The method of claim 23, wherein the ion exchange chromatography is performed by HPLC, and wherein the labeled unbound polymers are detected as they exit an ion exchange column.

27. The method of claim 18, wherein the polymer is an oligonucleotide.

28. A method for measuring the effect of altering a polymer array synthesis protocol, comprising:
(i) synthesizing a preselected array of diverse polymers occupying different regions on a solid support by a first synthesis protocol, wherein the diverse polymers are spatially defined on the solid support on which the preselected array is synthesized, thereby creating a reference array of polymers;
(ii) synthesizing a preselected array of diverse polymers occupying different regions on a solid support synthesized by a second synthesis protocol, wherein the diverse polymers are spatially defined on the solid support on which the preselected array is synthesized, and wherein the second synthesis protocol is different than the first synthesis protocol, thereby creating a test array of polymers;
(iii) cleaving separately the reference array of polymers and the test array of polymers, thereby creating a mixture of diverse cleaved polymers from the reference array and a mixture of diverse cleaved polymers from the test array;
(iv) comparing a measurement of presence of diverse cleaved polymers from the test array as an indicator of the efficiency of the second synthesis procedure with a measurement of presence of the mixture of diverse cleaved polymers from the reference array as an indicator of the efficiency of the first synthesis procedure, thereby determining whether a difference between the first and second synthesis procedures affects the efficiency of the second synthesis procedure.

29. The method of claim 28, wherein the test and reference polymers are oligonucleotides.

30. The method of claim 28, wherein the first synthesis protocol differs from the second synthesis protocol by a single variation.

31. The method of claim 28, wherein the reference polymers and the test polymers are attached to the solid substrate by a cleavable linker.

32. The method of claim 28, wherein the test and reference polymers comprise a detectable label.

33. The method of claim 32, wherein the label is a single isomeric label.

34. The method of claim 32, wherein the detectable label comprises a fluorescent moiety.

* * * * *